US006994959B1

(12) United States Patent
Tam

(10) Patent No.: US 6,994,959 B1
(45) Date of Patent: Feb. 7, 2006

(54) G-RICH OLIGO APTAMERS AND METHODS OF MODULATING AN IMMUNE RESPONSE

(75) Inventor: Robert Tam, Irvine, CA (US)

(73) Assignee: Valeant Research & Development, Costa Mesa, CA (US)

( * ) Notice: Subject to any disclaimer, the term of this patent is extended or adjusted under 35 U.S.C. 154(b) by 0 days.

(21) Appl. No.: 09/331,204

(22) PCT Filed: Dec. 19, 1997

(86) PCT No.: PCT/US97/23927

§ 371 (c)(1),
(2), (4) Date: Aug. 20, 1999

(87) PCT Pub. No.: WO98/29430

PCT Pub. Date: Jul. 9, 1998

(51) Int. Cl.
*A61K 48/00* (2006.01)
*C12Q 1/68* (2006.01)

(52) U.S. Cl. .............................. 435/6; 514/44; 435/325; 435/375; 536/23.1; 536/24.5

(58) Field of Classification Search .................. 514/44; 536/23.1, 24.5
See application file for complete search history.

(56) References Cited

U.S. PATENT DOCUMENTS 5,567,604 A * 10/1996 Rando et al. ............... 435/238
5,932,556 A * 8/1999 Tam ............................ 435/375

FOREIGN PATENT DOCUMENTS

WO   WO 96/24380   * 8/1996   .................. 514/44

OTHER PUBLICATIONS

Patel, D.J. et al. (1997) J. Mol Biol. 272;645-664.*
Smith et al. (1991) Nature 356; 164-168.*
Branch, A. D., (1998). Trends Biochem Sci. Feb. 1998;23 (2):45-50.*
Braasch, D. A. Biochemistry. Apr. 2002; 41(14): 4503-4510.*
Agrawal, S. Trends Biotechnol. Oct. 1996;14(10):376-87.*
Sharma H.W. et al., (1996) Anticancer Research 16; 61-70.*
Schultze et al. Structure 1994. 2:221-233.*
Kuramoto et al. Jpn. J. Cancer Res. 1992. 83:1128-1131.*

* cited by examiner

*Primary Examiner*—J. D. Schultz
(74) *Attorney, Agent, or Firm*—Brown Raysman Millstein Felder & Steiner LLP

(57) ABSTRACT

Aptamer oligonucleotides specifically bind to the DNA binding site of proteins such as Sp1 and Sp1-related proteins which regulate the genes which encode costimulatory molecules such as CD28 and cytokines such as IL-2 and GMCSF. The oligonucleotides compete with the DNA-binding sites of regulatory proteins which specifically regulate molecules to modulate T-cell activation. This serves to modulate gene expression by preventing transcription of the gene. Aptamers are administered to provide therapies for diseases which involve aberrant T-cell activation such as psoriasis, Type I (insulin-dependent) diabetes mellitus, multiple sclerosis, autoimmune uveitis, rheumatoid arthritis, systemic lupus erythematosus, inflammatory bowel disease (Crohn's and ulcerative colitis), and septic shock and to regulate normal T-cell activation such as in allograft rejection.

11 Claims, 6 Drawing Sheets

SEQUENCE LISTING

<160> NUMBER OF SEQ ID NOS: 28

<210> SEQ ID NO 1
<211> LENGTH: 30
<212> TYPE: DNA
<213> ORGANISM: synthetic construct

<400> SEQUENCE: 1
gggttcctcg gggaggaggg gctggaaccc                                   30

<210> SEQ ID NO 2
<211> LENGTH: 15
<212> TYPE: DNA
<213> ORGANISM: synthetic construct

<400> SEQUENCE: 2
ggagcacagg gtgct                                                   15

<210> SEQ ID NO 3
<211> LENGTH: 15
<212> TYPE: DNA
<213> ORGANISM: synthetic construct

<400> SEQUENCE: 3
tcatcacagg gtgct                                                   15

<210> SEQ ID NO 4
<211> LENGTH: 18
<212> TYPE: DNA
<213> ORGANISM: synthetic construct

<400> SEQUENCE: 4
ttggaggggg tggtgggg                                                18

<210> SEQ ID NO 5
<211> LENGTH: 18
<212> TYPE: DNA
<213> ORGANISM: synthetic construct

<400> SEQUENCE: 5
ggggaggagg ggctggaa                                                18

<210> SEQ ID NO 6
<211> LENGTH: 21
<212> TYPE: DNA

```
<213> ORGANISM: synthetic construct

<400> SEQUENCE: 6
gggttggagg gggtggtggg g                                      21

<210> SEQ ID NO 7
<211> LENGTH: 18
<212> TYPE: DNA
<213> ORGANISM: synthetic construct

<400> SEQUENCE: 7
ttggaggggg aggagggg                                          18

<210> SEQ ID NO 8
<211> LENGTH: 18
<212> TYPE: DNA
<213> ORGANISM: synthetic construct

<400> SEQUENCE: 8
ttggaggggg aggtgggg                                          18

<210> SEQ ID NO 9
<211> LENGTH: 18
<212> TYPE: DNA
<213> ORGANISM: synthetic construct

<400> SEQUENCE: 9
ttggaggcgg tggtggcg                                          18

<210> SEQ ID NO 10
<211> LENGTH: 18
<212> TYPE: DNA
<213> ORGANISM: synthetic construct

<400> SEQUENCE: 10
ttggagccgg tggtggcc                                          18

<210> SEQ ID NO 11
<211> LENGTH: 18
<212> TYPE: DNA
<213> ORGANISM: synthetic construct

<400> SEQUENCE: 11 ttggagggc tcctcggg                                           18

<210> SEQ ID NO 12
<211> LENGTH: 16
<212> TYPE: DNA
<213> ORGANISM: synthetic construct

<400> SEQUENCE: 12
ttggagccgg tggtgg                                            16

<210> SEQ ID NO 13
<211> LENGTH: 12
<212> TYPE: DNA
<213> ORGANISM: synthetic construct

<400> SEQUENCE: 13
ggggtggtgg gg                                                12

<210> SEQ ID NO 14
<211> LENGTH: 10
```

```
<212> TYPE: DNA
<213> ORGANISM: synthetic construct

<400> SEQUENCE: 14
ggggttgggg                                                              10

<210> SEQ ID NO 15
<211> LENGTH: 5
<212> TYPE: DNA
<213> ORGANISM: synthetic construct

<400> SEQUENCE: 15 tgggg                                                                    5

<210> SEQ ID NO 16
<211> LENGTH: 4
<212> TYPE: DNA
<213> ORGANISM: synthetic construct

<400> SEQUENCE: 16 gggg                                                                     4

<210> SEQ ID NO 17
<211> LENGTH: 20
<212> TYPE: DNA
<213> ORGANISM: synthetic construct

<400> SEQUENCE: 17
cactgcgggg agggctgggg                                                   20

<210> SEQ ID NO 18
<211> LENGTH: 20
<212> TYPE: DNA
<213> ORGANISM: synthetic construct

<400> SEQUENCE: 18
atggggtgca caaactgggg                                                   20

<210> SEQ ID NO 19
<211> LENGTH: 15
<212> TYPE: DNA
<213> ORGANISM: synthetic construct

<400> SEQUENCE: 19
aacgttgagg ggcat                                                        15

<210> SEQ ID NO 20
<211> LENGTH: 18
<212> TYPE: DNA
<213> ORGANISM: synthetic construct

<400> SEQUENCE: 20
ttccagcccc tcctcccc                                                     18

<210> SEQ ID NO 21
<211> LENGTH: 18
<212> TYPE: DNA
<213> ORGANISM: synthetic construct

<400> SEQUENCE: 21
aacctccccc accacccc                                                     18

<210> SEQ ID NO 22
```

```
<211> LENGTH: 22
<212> TYPE: DNA
<213> ORGANISM: synthetic construct

<400> SEQUENCE: 22
attcgatcgg ggcggggcga gc                                               22

<210> SEQ ID NO 23
<211> LENGTH: 21
<212> TYPE: DNA
<213> ORGANISM: synthetic construct

<400> SEQUENCE: 23
cgcttgatga gtcagccgga a                                                21

<210> SEQ ID NO 24
<211> LENGTH: 26
<212> TYPE: DNA
<213> ORGANISM: synthetic construct

<400> SEQUENCE: 24
gatcgaactg accgcccgcg gcccct                                           26

<210> SEQ ID NO 25
<211> LENGTH: 22
<212> TYPE: DNA
<213> ORGANISM: synthetic construct

<400> SEQUENCE: 25
agttgagggg actttcccag gc                                               22

<210> SEQ ID NO 26
<211> LENGTH: 22
<212> TYPE: DNA
<213> ORGANISM: synthetic construct

<400> SEQUENCE: 26
tgtcgaatgc aaatcactag aa                                               22

<210> SEQ ID NO 27
<211> LENGTH: 27
<212> TYPE: DNA
<213> ORGANISM: synthetic construct

<400> SEQUENCE: 27
agagattgcc tgacgtcaga gagctag                                          27

<210> SEQ ID NO 28
<211> LENGTH: 25
<212> TYPE: DNA
<213> ORGANISM: synthetic construct

<400> SEQUENCE: 28
gcagagcata taaggtgagg tagga                                            25
```

G-RICH OLIGO APTAMERS AND METHODS OF MODULATING AN IMMUNE RESPONSE

FIELD OF THE INVENTION

The field of the invention is immunology.

BACKGROUND OF THE INVENTION

The pathogenesis and exacerbation of many prevalent T-cell mediated diseases result from an inappropriate immune response driven by abnormal T-cell activation. A number of other diseases are thought to be caused by aberrant T-cell activation including Type I (insulin-dependent) diabetes mellitus, thyroiditis, sarcoidosis, multiple sclerosis, autoimmune uveitis, rheumatoid arthritis, systemic lupus erythematosus, inflammatory bowel disease (Crohn's and ulcerative colitis) and aplastic anemia. In addition, a variety of syndromes including septic shock and tumor-induced cachexia may involve T-cell activation and augmented production of potentially toxic levels of lymphokines. Normal T-cell activation also mediates the rejection of transplanted cells and organs by providing the neccessary signals for the effective destruction of the "foreign" donor tissue.

The activation of T-lymphocytes leading to T-cell proliferation and gene expression and secretion of specific immunomodulatory cytokines requires two independent signals. The first signal involves the recognition, by specific T-cell receptor/CD3 complex, of antigen presented by major histocompatibility complex molecules on the surface of antigen-presenting cells (APCs). Antigen-nonspecific intercellular interactions between T-cells and APCs provide the second signal which serves to regulate T-cell responses to antigen. These secondary or costimulatory signals determine the magnitude of a T-cell response to antigen. Costimulated cells react by increasing the levels of specific cytokine gene transcription and by stabilizing selected mRNAs. T-cell activation in the absence of costimulation results in an aborted or anergic T-cell response. One key costimulatory signal is provided by interaction of the T-cell surface receptor CD28 with B7-related molecules on APC (Linsley and Ledbetter (1993) *Annu Rev Immunol* 11: 191–212). CD28 is constitutively expressed on 95% of CD4+ T-cells (which provide helper functions for B-cell antibody production) and 50% of CD8+ T-cells (which have cytotoxic functions) (Yamada et al (1985) *Eur J Immunol* 15: 1164–1168). Following antigenic or in vitro mitogenic stimulation, further induction of surface levels of CD28 occurs, as well as the production of certain immunomodulatory cytokines. These include interleukin-2 (IL-2), required for cell cycle progression of T-cells, interferon-gamma (IFNγ), which displays a wide variety of anti-viral and anti-tumor effects and interleukin-8 (IL-8), known as a potent chemotactic factor for neutrophils and lymphocytes. These cytokines have been shown to be regulated by the CD28 pathway of T-cell activation (Fraser et al (1991) *Science* 251: 313–316, Seder et al (1994) *J Exp Med* 179: 299–304, Wechsler et al (1994) *J Immunol* 153: 2515–2523). IL-2, IFNγ and IL-8 are essential in promoting a wide range of immune responses and have been shown to be overexpressed in many T-cell mediated disease states.

In psoriasis, activated lesional T-cells predominantly release Th1 cytokines such as IL-2 and IFNγ (Schlaak et al (1994) *J Invest Derm* 102: 145–149). These secreted cytokines induce normal keratinocytes to express the same phenotype (HLA DR+/ICAM-1+) as found in psoriasis lesions (Baadsgaard et al (1990) *J Invest Derm* 95: 275–282). Also IL-8, by virtue of its in vitro and in vivo proinflammatory properties and because it is secreted in large amounts by both activated T-cells and keratinocytes from psoriatic lesions, is considered a major contributor to the pathologic changes seen in psoriatic skin such as keratinocyte hyperproliferation. Furthermore, one of the B7 family of receptors (the natural ligands for CD28 found on activated APC), BB1 has been shown to be expressed in psoriatic but not unaffected skin keratinocytes (Nickoloff et al (1993) *Am J Pathology* 142: 1029–1040) underscoring the importance of T-cell activation in pathogenesis of the disease.

In other T-cell mediated skin disorders such as allergic contact dermatitis and lichen planus, CD28 was expressed in high levels in the majority of dermal and epidermal CD3+ T-cells, but in normal skin and basal cell carcinoma (a non T-cell mediated skin disease), CD28 was expressed only in perivascular T-cells. Similarly, in both allergic contact dermatitis and lichen planus, B7 expression was found on dermal dendritic cells, dermal APCs and on keratinocytes, but not in normal skin and basal cell carcinoma (Simon et al (1994) *J Invest Derm* 103: 539–543). Therefore this suggests that the CD28/B7 pathway is an important mediator of T-cell-mediated skin diseases.

Aberrant T-cell activation associated with certain autoimmune diseases caused by the loss of self-tolerance is predominantly characterized by the presence of CD28+T-cells and expression of its ligand, B7 on activated professional APCs (monocyte, macrophage or dendritic cells). These include autoimmune Graves thyroiditis (Garcia-Cozar et al (1993) *Immunologia* 12 32), sarcoidosis (Vandenberghe et al (1993) *Int Immunol* 5: 317–321), rheumatoid arthritis (Verwilghen et al (1994) *J Immunol* 153: 1378–1385) and systemic lupus erythematosus (Sfikakis et al (1994) *Clin Exp Immunol* 96: 8–14). In normal T-cell activation, which mediates the rejection of transplanted cells and organs, the binding of CD28 by its appropriate B7 ligand during T-cell receptor engagement is critical for proper allogeneic response to foreign antigens, for example, on donor tissue (Azuma et al (1992) *J Exp Med* 175: 353–360, Turka et al (1992) *Proc Nat Acad Sci USA* 89: 11102–11105).

Traditional therapies for autoimmune diseases do not prevent T-cell activation; the effector step in the autoreactive immune responses to self-antigen. Drugs, such as steroids and non-steroid anti-inflammatory drugs (NSAIDS), are currently used to ameliorate symptoms, but they do not prevent the progression of the disease. In addition, steroids can have side effects such as inducing osteoporosis, organ toxicity and diabetes, and can accelerate the cartilage degeneration process and cause so-called post-injection flares for up to 2 to 8 hours. NSAIDS can have gastrointestinal side effects and increase the risk of agranulocytosis and iatrogenic hepatitis.

Immunosuppressive drugs are also used as another form of therapy, especially in advanced disease stages. However, these drugs suppress the entire immune system and often treatment has severe side effects including hypertension and nephrotoxicity. Also established immunosuppressants such as cyclosporin and FK506 cannot inhibit the CD28-dependent T-cell activation pathway (June et al (1987) *Mol Cell Biol* 7: 4472–4481).

Current agents which affect T-cell activation include synthetic peptides, monoclonal antibodies and soluble forms of T-cell activation molecules. To date competitive synthetic peptides to T-cell activation molecules such as CD28, CD40L and the CAM family of adhesion molecules have not been identified. Monoclonal antibodies (mAb) have been shown to have possible therapeutic effect in such T-cell mediated diseases such as psoriasis (anti-CD4 (Prinz et al (1994) *Lancet* 338: 320–321)) and immununosuppression of normal T-cell activation in allografts (anti-VCAM-1 and VLA-4 (Isobe et al (1994) *J Immunol* 153: 5810–5818)). However, with chronic treatment, the host animal develops antibodies against the monoclonal antibodies thereby limiting their usefulness. 'Humanized' monoclonal antibodies, have been developed which apparently reduce the risk of an induced immune response to these mAbs. However, these are still under development and in addition, these new mAbs remain large proteins and therefore may have difficulty reaching their target sites. Soluble forms of T-cell activation molecules such as CTLA-4Ig, containing the extracellular domain of the human CTLA-4 gene (which is sequentially related to CD28), fused to a human Ig Cγ chain, have been developed. CTLA-4Ig has been shown to specifically block normal T-cell activation by preventing rejection of xenogeneic (Lenschow et al (1992) *Science* 257: 789–792) and allogeneic (Turka et al (1992) *Proc Nat Acad Sci USA* 89: 11102–11105) cardiac allografts in rats and have therapeutic effect on aberrant T-cell activation such as found in rat autoimmune glomerulonephritis (Nishikawa et al (1994) *Eur J Immunol* 24: 1249–1254). Soluble CTLA-4Ig however suffers from similar limitations as monoclonal antibodies in addition to the expense of their production. Also the true function of this CD28-like molecule is not known therefore this needs to be fully determined before any therapeutic benefit can be evaluated.

Inhibition of the cell-surface expression of CD28 leads to prolonged unresponsiveness or deletion of activated T-cells. Inactivation prevents T-cell proliferation and arrest of T-cell-specific production of specific immunoregulatory cytokines such as interleukin-2, interferon-gamma and interleukin-8.

Regulation of CD28 gene expression can be achieved using antisense and triplex-forming oligonucleotides by hybridizing oligodeoxy-ribonucleotides or oligoribonucleotides to DNA or RNA sequences within the CD28 gene or promoter region (See PCT/US96/01507, filed Aug. 30, 1996). Oligonucleotides avoid many of the pitfalls of current agents used to block the effects of normal and abnormal T-cell activation. However, these oligos designed for antisense strategies are susceptible to degradation by intracellular nucleases or nucleases present in the extracellular milieu.

The binding of DNA (or RNA) to protein has been shown previously to be a fundamental pathway by which transcription of a gene is controlled. These regulatory proteins or transcription factors recognize DNA sequences with specific secondary structure and the ensuing interaction can lead to positive or negative control of gene expression. Aptamers are short oligonucleotide sequences which can specifically bind specific proteins. It has been demonstrated that different aptameric sequences can bind specifically to different proteins, for example, the sequence GGNNGG where N=guanosine (G), cytosine (C), adenosine (A) or thymidine (T) binds specifically to thrombin (Bock et al (1992) Nature 355: 564–566 and U.S. Pat. No. 5,582,981 (1996) Toole et al).

Aptameric sequences have not been described, however, which can function as competitive inhibitors of DNA-binding sites on regulatory proteins known as transcription factors. Transcription factors are a class of proteins which regulate genes by primarily binding to specific regulatory sequences in the 5' upstream promoter region of those genes. This interaction leads to initiation of transcription. Certain transcription factors such as Sp1, AP2, AP-1, EGR-1 and NFκB are critical in the activation of T and B lymphocytes (Skerka et al *J Biol Chem* 270: 22500–22506, Jung et al (1995) *Ann N Y Acad Sci* 766: 245–252). In some cases these transcription factors are induced by signals initiated following costimulation (Jung et al (1995) *Ann N Y Acad Sci* 766: 245–252). Thus, there is still a need to develop agents and methods for interfering with the interaction of protein with specific DNA binding sites which would lead to suppression of certain immune pathways including the costimulatory pathway.

SUMMARY OF THE INVENTION

The present invention provides aptamers having a length of between about 12 and 22 nucleic acid units, inclusive, and a sequence which includes at least two G-rich regions selected from the group consisting of GGnG, GGGG, GnGG, nGGG and GGGn, where G is guanidine and n is any nucleotide.

In preferred embodiments, the oligonucleotides are designed to bind to specific regulatory proteins such as Sp1 and Sp1-related proteins and act to compete with the binding of these transcription factors to the promoter region of the genes which are under their control. This serves to modulate gene expression by preventing transcription of the gene. Thus the aptamer oligonucleotides are able to inhibit the function of RNA or DNA, either its translation into protein, its translocation into the cytoplasm or any other activity neccessary to its overall biological function. The failure of the RNA or DNA to perform all or part of its function results in failure of a portion of the genome controlling T-cell activation to be properly expressed, thus modulating said metabolism.

It is preferred to target aptameric nucleic acid decoys to compete with the DNA-binding sites of regulatory proteins which specifically regulate molecules which can modulate T cell activation. It has been discovered that the CD28 protein is particularly useful for this approach. Inhibition of CD28 and CD28-related gene expression is expected to be useful for the treatment of psoriasis and other skin diseases, syndromes with aberrant T-cell activation, autoimmune disorders and allograft rejection.

Methods of modulating T-cell activation comprising contacting a patient with an oligonucleotide which competes with the DNA-binding site of a regulatory protein such as to inhibit expression of a regulated protein known to be capable of modulating T-cell activation. Oligonucleotides which bind to proteins such as Sp1 and Sp1-related proteins which regulate transcription of CD28 and CD28-related genes are preferred.

In another aspect of the invention, aptamers are administered to provide therapies for diseases which involve aberrant T-cell activation such as psoriasis, AIDS-exacerbated psoriasis and other skin diseases, Type I (insulin-dependent) diabetes mellitus, thyroiditis, sarcoidosis, multiple sclerosis, autoimmune uveitis, rheumatoid arthritis, systemic lupus erythematosus, inflammatory bowel disease (Crohn's and ulcerative colitis), septic shock, tumor-induced cachexia and aplastic anemia and to regulate normal T-cell activation such as in allograft rejection. This can be achieved by perturbation in the synthesis and expression of T-cell activation molecules including CD28 and CD28-related molecules.

In yet another aspect of the invention, aptamers are provided which are capable of binding specific regulatory proteins such as Sp1 and Sp 1-related proteins and thus inhibit transcription of genes such as CD28 and CD28- related proteins which a) are normally regulated by these proteins and b) can modulate T cell responses.

DETAILED DESCRIPTION OF SPECIFIC EMBODIMENTS

Figure 1A:
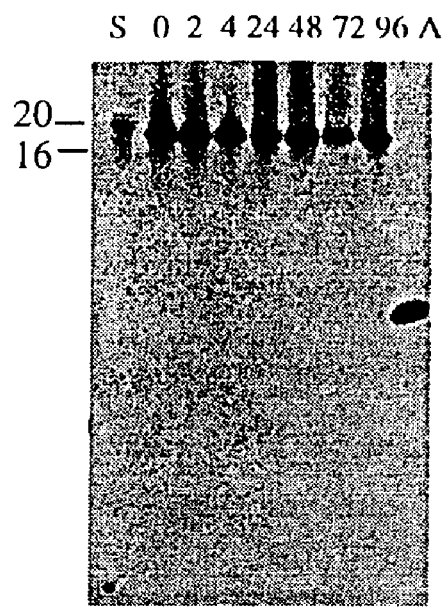
FIGS. 1A and 1B are graphical representations of the in vitro stability of $^{32}$P-labeled phosphorothioate, ICN 16064 (Seq #4), in extracellular fluid and in Jurkat cells, respectively.

Aptameric oligonucleotides that specifically bind to the DNA-binding site of regulatory proteins such as Sp1 and Sp1-related proteins will prevent the binding of the regulatory protein with specific double-stranded region of DNA in the promoter region the gene of interest. The competive binding by the aptamer would hinder transcription of the gene and thus inhibit the flow of genetic information from DNA to protein. The properties of oligonucleotides which make them specific for their target also make them versatile. Because oligonucleotides are long chains of four monomeric units they may be readily synthesized for any target RNA sequence.

Oligonucleotide-mediated inhibition of gene expression has been demonstrated in many model and in vitro systems and has therapeutic potential as a new strategy for treating many human diseases (Uhlmann and Peyman (1990) *Chem Rev* 90: 544–584, Zon and Stec (1991) *Oligonucleotides and analogues—A Practical Approach:* 87–108, Miller et al (1981) *Biochem* 20: 1874–1880, Orson et al (1991) *Nucleic Acid Res* 19: 3435–3441, Helene and Toulme (1990) *Biochem Biophys Acta* 1049: 99–125, Thierry and Dritschilo (1992) *Nucleic Acid Res* 20: 5691–5698). Because of recent advances in synthesis of nuclease resistant oligonucleotides, including phosphorothioates Zon and Stec (1991) *Oligonucleotides and analogues—A Practical Approach:* 87–108 and phosphorothioate-3'hydroxypropylamine (Tam et al (1994) *Nucleic Acid Res* 22: 977–986), which exhibit enhanced cell uptake, it is now possible to consider the use of oligonucleotides as a novel form of therapeutics. Aptameric oligonucleotides targeting regulatory protein binding sites represent an alternative class of nucleic acid-based compounds and they offer an ideal solution to the problems encountered in prior art approaches. They are directly involved in the modulation of specific gene expression and so switch off target protein expression and not the competitive inhibition of soluble receptors to the target protein, an interaction which requires a complete understanding of the binding mechanisms and affinity of receptor-ligand interaction. Oligonucleotides are small molecules and therefore do not encounter the same steric problems as large molecule inhibitors.

Description of Targets

Targets comtemplated herein include molecules which can be regulated by transcription factors which play an essential role in initiating or maintaining an immune response. These include the costimulatory molecules such as CD28 and cytokines such as IL-2, GM-CSF and IFNγ.

For therapeutics, an animal suspected of having a disease which can be treated by decreasing the expression of costimulatory molecules such as CD28 or CD28-related molecules can be treated by administering oligonucleotides in accordance with this invention. Oligonucleotides may be formulated in a pharmaceutical composition, which may include carriers, thickeners, diluents, buffers, preservatives, surface active agents, liposomes or lipid formulations and the like in addition to the oligonucleotide. Pharmaceutical compositions may also include one or more active ingredients such as antimicrobial agents, anti-inflammatory agents, anesthetics, and the like in addition to oligonucleotide.

The pharmaceutical composition may be administered in a number of ways depending on whether local or systemic treatment is desired, and on the area to be treated. Administration may be topically (including opthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be neccessary or desirable. Coated condoms or gloves may also be useful.

Compositions for oral administration include powders or granules, suspensions or solutions in water or non-aqueos media, capsules, sachets or tablets. Thickeners, flavorings, diluents, emulsifiers, dispersing aids or binders may be desirable.

Formulations for parenteral administration may include sterile aqueous solutions which may contain buffers, liposomes diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

In a preferred systemic application, the aptamers are to be administered intravenously in a dose of 5 mg/kg once per day. In a preferred topical application, the aptamers are to be administered in a 1–5% solution once per day. In a preferred pulmonary application, the aptamers are to be administered in an aerosolized dose of 5 mg once per day.

The present invention employs aptameric oligonucleotides for use in inhibition of the function of RNA and DNA corresponding to proteins capable of modulating T-cell activation. In the context of this invention, the term 'oligonucleotide' refers to an oligomer or polymer of ribonucleic acid or deoxyribonucleic acid. This term includes oligomers consisting of naturally occurring bases, sugars and inter-sugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

The oligonucleotides in accordance with this invention preferably comprise from about 3 to about 50 nucleic acid base units. It is more preferred that such oligonucleotides comprise from about 8 and 30 nucleic acid base units, and still more preferred to have from about 12 and 22 nucleic acid base units. As will be appreciated, a nucleic acid base unit is a base-sugar combination suitably bound to an adjacent nucleic acid base unit through phosphodiester or the other bonds.

The oligonucleotides used in accordance with this invention may be conveniently and routinely made through the well-known technique of solid phase synthesis. Several vendors including Applied Biosystems sell equipment for such synthesis. Any other means for such synthesis may also be employed, however the actual synthesis of oligonucleotides are well within the talents of the routineer. It is also well known to use similar techniques to prepare other oligonucleotides such as phosphorothioates and 3'amine-phosphorothioates.

In accordance with this invention, persons of ordinary skill in the art will understand that messenger RNA identified by the open reading frames (ORFs) of the DNA from which they are transcribed includes not only the information from the ORFs of the DNA, but also associated ribonucleotides which form regions known to such persons as the 5'-untranslated, the 3'-untranslated region and intervening sequence ribonucleotides. Thus, oligonucleotides may be formulated in accordance with this invention which are targeted wholly or in part to these associated ribonucleotides as well as to the informational ribonucleotides. In preferred embodiments, the aptameric oligonucleotide interacts with the DNA-binding site of a regulatory protein such as Sp1 and Sp1-related proteins, and in doing so interrupt the expression of a gene encoding a protein involved in T-cell activation. In preferred embodiments, said proteins to be regulated are CD28 and all homologues of the CD28 molecule. Oligonucleotides comprising sequences containing at least two G-rich regions defined as a region of four nucleotides containing at least three guanosine (G) residues such as GGGG, GNGG, GGNG where N=A, C, G, U or T are preferred. Two such G-rich regions separated by at most 6 residues and preferably 4 or fewer residues are useful in the invention. preferred sequence segments which may be useful in whole or in part are:

| 5' | 3' | SEQ ID |
|---|---|---|
| TTG GAG GGG GTG GTG GGG | | FIG. 1A |
| GGG GAG GAG GGG CTG GAA | | ICN 16481 |
| GGG GTG GTG GGG | | ICN 16525 |
| TTG GAG GGG GAG GAG GGG | | ICN 16475 |
| TTG GAG GGG GAG GTG GGG | | ICN 16479 |
| GGG TTG GAG GGG GTG GTG GGG | | ICN 16065 |

While the illustrated sequences are believed to be accurate, the present invention is directed to the correct sequences should errors be found. Oligonucleotides useful in the invention comprise one of these sequences, or part thereof. Thus, it is preferred to employ any of these oligonucleotides as set forth above, or any of the similar oligonucleotides which persons of ordinary skill in the art can prepare from knowledge of the preferred oligonucleotide targets for the modulation of the synthesis of T-cell activation molecules including CD28 and CD28-related molecules. The inhibition or modulation of production of the CD28 and/or CD28 homologues are expected to have significant therapeutic benefits in the treatment of disease. In order to assess the effectiveness of the compositions, an assay or series of assays is required.

EXAMPLES

Oligonucleotides

Oligodeoxynucleotides were synthesized on an automated DNA synthesizer (Applied Biosystems model 394) using standard phosphoramidite chemistry. β-cyanoethylphosphoramidites, synthesis reagents and CPG polystyrene columns were purchased from Applied Biosystems (ABI, Foster City, Calif.). 3'-Amino-Modifier C3 CPG columns were purchased from Glen Research (Sterling, Va.). For phosphorothioate oligonucleotides, the standard oxidation bottle was replaced with tetraethylthiuram disulfide/acetonitrile, and the standard ABI phosphorothioate program was used for the stepwise addition of phosphorothioate linkages. After cleavage from the controlled pore glass column, the protecting groups were removed by treating the oligonucleotides with concentrated ammonium hydroxide at 55° C. for 8 hours. The oligonucleotides were purified by HPLC using a reverse phase semiprep C8 column (ABI). Following cleavage of the DMT protecting group, treatment with 80% acetic acid and ethanol precipitation, the purity of the product was assessed by HPLC using an analytical C18 column (Beckman, Fullerton, Calif.). All oligonucleotides of >90% purity were lyophilized to dryness. Oligonucleotides were reconstituted in sterile deionized water (ICN, Costa Mesa), adjusted to 400 μM following evaluation of $OD_{260nm}$, aliquoted and stored at −20° C. prior to experimentation. In all cases, at least three batches of each oligonucleotide listed in Table 1 were used.

In Vitro Oligonucleotide Stability Studies

Temporal oligonucleotide stability analyses were performed as described previously (Tam et al (1994) *Nucleic Acid Res* 22: 977–986). Oligonucleotide degradation profiles were assessed by electrophoresis and quantitated using Nickspin columns.

Cell Lines and T Cell Purification

Peripheral blood mononuclear cells (PBMCs) were isolated from the buffy coat following Ficoll-Hypaque density gradient centrifugation of 60 ml blood from healthy donors. T-cells were then purified from the PBMCs using Lymphokwik lymphocyte isolation reagent specific for T-cells (LK-25T, One Lambda, Canoga Park Calif.). An average yield of 40–60×10$^6$ T-cells were then incubated overnight at 37° C. in 20–30 ml RPMI-AP5 (RPMI-1640 medium (ICN, Costa Mesa, Calif.) containing 20 mM HEPES buffer, pH 7.4, 5% autologous plasma, 1% L-glutamine, 1% penicillin/streptomycin and 0.05% 2-mercaptoethanol) to remove any contaminating adherent cells. In all experiments, T-cells were washed with RPMI-AP5 and then plated on 96-well microtitre plates at a cell concentration of 2–3×10$^6$ cells/ml.

The T-cell lymphoma cell line, Jurkat E6-1 (CD28$^+$/CD4$^+$) cells (152-TIB) were maintained in RPMI-10 (RPMI-1640 medium containing 20 mM HEPES buffer, pH 7.4, 10% fetal calf serum (FCS) (Hyclone, Logan, Utah), 1% L-glutamine and 1% penicillin/streptomycin).

Mitogen-Induced T-Cell Activation and Oligonucleotide Treatment

Prior to the addition of human peripheral T-cells or T-cell lymphoma cell lines (0.2–0.3×10$^6$), duplicate 96-well microtitre plates were pre-coated with purified anti-CD3 monoclonal antibody (mAb) (6.25–200 ng/well) (clone HIT 3a, Pharmingen, San Diego, Calif.) and washed twice with cold phosphate-buffered saline, pH 7.4 (PBS). Anti-CD3 mAb-treated T-cells were further activated by the addition of 2 ng phorbol 12-myristate 13-acetate (PMA) (Calbiochem, La Jolla, Calif.) and incubated for 48 h at 37° C. Anti-CD3/PMA-activated T-cells were treated with 1–20 μM CD28-specific and control oligonucleotides immediately following activation and re-treated 24 h later. T-cells from one duplicate plate was used for immunofluorescence analysis and the 1A used for cytokine studies and the second plate was used for T-cell proliferation analysis.

Immunofluorescence Studies

Following activation, 150 μl cell supernatant from the first duplicate microplate was transferred to another microplate for analysis of cell-derived cytokine production. The remaining cells were washed twice with isotonic saline solution, pH 7.4 (Becton Dickinson, Mansfield, Mass.) and resuspended in 50 μl isotonic saline solution and split into two samples. One sample aliquot was co-stained with either PE-CD28/FITC-CD4 mAb and non-specific fluorescence was assessed by staining the second aliquot with PE/FITC-labeled isotype-matched control monoclonal antibody. All fluorescence-labeled monoclonal antibodies were obtained from Becton Dickinson (San Jose, Calif.). Incubations were performed in the dark at 4° C. for 45 min using saturating mAb concentrations. Unincorporated label was removed by washing in PBS prior to the analysis with a FACScan flow cytometer (Becton Dickinson). Antigen density was indirectly determined in gated live cells and expressed as the mean channel of fluorescence (MCF). Surface expression of the CD4$^+$-subset of cells stained with CD28 mAb was determined by subtracting the MCF of CD28$^+$CD4$^+$ from the MCF of CD28$^-$CD4$^-$ cells. The viability of control untreated and oligonucleotide-treated cells were determined in each batch of all oligonucleotides in multiple donors by staining with the vital dye, propidium iodide (5 μg/ml final concentration). The percentage of live cells which excluded propidium iodide was determined by flow cytometry and was >90% (range 90–99%) following treatment with all batches of all oligonucleotides at a dose range of 1–20 μM.

Cytokine Analyses

Cell-derived human cytokine concentrations were determined in cell Supernatants from the first duplicate microplate. Mitogen-induced changes in interleukin-2 (IL-2) levels were determined using a commercially available ELISA kit (R & D systems Quantikine kit, Minneapolis, Minn.) All ELISA results were expressed as pg/ml.

Electrophoretic Mobility Shift Analyses (EMSA)

Test oligonucleotides were labeled at the 5' end with [γ-32P]-ATP (ICN, Costa Mesa, Calif.) using T4 polynucleotide kinase as per manufacturers protocol (Gibco BRL, Gaithersburg, Md.). 10 μg of HeLa cell nuclear extract (Promega) was incubated with approximately 80,000 cpm of labeled oligonucleotide for 20 min at room temperature. The binding reaction mixtures contained 10 mM Tris-HCl (pH 7.5), 50 mM NaCl, 0.5 mM DTT, 0.5 mM EDTA, 1 mM MgCl$_2$, 4% glycerol and 0.5 μg of poly(dI.dC). DNA-protein complexes were resolved by electrophoresis through a 4% polyacrylamide gel containing 0.5×TBE buffer (50 mM Tris, 45 mM boric acid, 0.5 mM EDTA) for approximately 3 hr at 100 V. The gel was dried and autoradiographed using Phosphorlmager (Biorad, Richmond, Calif.).

cDNA Preparation for DNase Footprint Assay and Gel Shift Assay

The cDNAs (about 300 base pairs) used in the protein-DNA binding in DNase footprint assays and gel shift assays were isolated from plasmids pCAT3e 28b, pCAT3e 28h or pCAT3e 28h-1. 60 μg of each plasmid were digested with BglII, some being put first on agarose gel to check for linearity, the rest then phenol/sevag extracted, ethanol precipitated and then resuspended in water and digested with SacI. Again, a small portion was put on the gel to check if it's cut. (2 bands should appear now: a 4 kb band and a 300 b.p. band.) The rest was phenol/sevag extracted and ethanol precipitated. For the following dephosphorylation, DNA pellet was resuspended in a small volume of water (62 μl), 1 μl of 20 U/μl alkaline phosphatase (Boehringer Mannheim, Indianapolis, Ind.) and 7 μl of the 10× reaction buffer were added. After incubating the reaction mixture at 37° C. for 1 hour, 7 μl of pH 8.0, 0.2M EGTA was added and the whole tube was heated at 65° C. for 10 min. The whole 77 μl of the dephosphorylated DNA were put on 1% agarose gel to purify the 300 b.p. band using Qiaquick gel extraction kit from Qiagen (Santa Clarita, Calif.). Final volume of the purified 300 b.p. band was 70 μl and its concentration was calculated as follows: 60 μg×(300 b.p./4300 b.p.)=4.2 μg, assuming 50% recovery after all these manipulations: 2.1 μg/70 μl=30 ng/μl. For each $^{32}$P end-labeling reaction (kinasing), 5 μl to 7 μl of the purified 300 b.p. DNA was used.

Polyacrylamide Gel Preparation for Gel Shift Assay

4% non-denaturing polyacrylamide gel solution in 0.5×TBE was prepared according to the Promega Gel Shift Assay Systems technical bulletin (4% acrylamide, 0.05% bisacrylamide, 2.5% glycerol, 0.5×TBE). A stock of 250 ml of the above gel solution was prepared, filtered and kept at 4° C. For each use, 12.5 μl of TEMED and 187.5 μl of 10% ammonium persulfate was added to every 25 ml of the stock 4% gel solution and poured into 16.5 cm×16.5 cm×0.75 mm glass plates. Gels were always allowed to polymerize overnight for optimal results. The gel was pre-run in 0.5×TBE buffer for 30 min at 100V before loading the samples.

Double Stranded Oligonucleotides Formation and Purification

The method used here was from "Antiparallel polypurine phosphorothioate oligonucleotides form stable triplexes with the rat α1(I) collagen gene promoter and inhibit transcription in cultured rat fibroblasts" by Jacob Joseph et al. in Nucleic Acids Research, 1997, Vol. 25, No. 11, 2182–2188.

Equal amounts of complementary single strands were heated at 80° C. for 5 min in 0.25M NaCl, followed by slow cooling to room temp. Annealed double-stranded oligonucleotides were purified by electrophoresis on a 6% non-denaturing (29:1) polyacrylamide gel, later cut out, "crushed and soaked," ethanol precipitated using the methods described in "Molecular cloning, a laboratory manual" by Sambrook, Fritsch & Maniatis. About 20 ng of d.s. oligo were used in each labeling reaction.

End $^{32}$P Labeling of DNA 150 to 200 ng of the 300 b.p. cDNA or 20 ng of the d.s. oligo were incubated with 10 $\mu$Ci of [$\gamma$-$^{32}$P] ATP (4500 Ci/mmole, ICN, Irvine, Calif.) and 10 U of kinase and 1× kinase buffer (both from Promega) in a 10 $\mu$l volume at 37° C. for 1 hour, and purified on Centri Spin-10 column (Princeton Separation, Adelphia, N.J.). About 80,000–100,000 cpm of kinased DNA was used in each gel shift reaction.

Gel Shift Assay

Proteins (nuclear extract or purified transcriptional factor) were incubated with 1× gel shift buffer (Promega, Madison, Wis.) at room temp for 5–10 min before kinased DNA was added and incubated for another 20–30 min at room temp. Samples were then loaded on the pre-run 4% non-denaturing gel. After about 3–4 hours run at 100V in 0.5×TBE, gel was dried on 2 pieces of Whatman papers and exposed in a phosphor-imager overnight.

Antibody Gel Supershift Assay

Antibody to Sp1 (clone 1C6, Santa Cruz Biotechnologies, Santa Cruz, Calif.) was pre-incubated with purified Sp1 (Promega) for 1 hour before the $^{32}$P-labeled cDNA or oligo was added.

Competition Gel Shift Assay

About 70–100 molar excess of non-labeled oligonucleotides (either single-stranded or double-stranded) were pre-incubated with protein at room temp for about 30 min before the $^{32}$P-labeled DNA was added.

The Construction of pCAT3e 28b, pCAT3e 28h, pCAT3e 28h-1

CD28 upstream cDNA (−197 to +28) was produced by RT PCR using Jurkat total RNA as template. This piece of cDNA was first cloned into a TA cloning vector PCR 2.1 (Invitrogen, Carlsbad, Calif.). The same cDNA was later subcloned into pCAT3e (Promega) by inserting into the XhoI-SacI site. pCAT3e 28h and pCAT3e 28h-1 are mutants of pCAT3e 28b in which −51 to −22 sequences were deleted and substituted by 15 other nucleotides.

Transfection (Transient Expression)

One day before transfection, Jurkat cells were prepared in 2 or 3 T150s at 1:4 or 1:5 dilutions from 80–90% confluent cells. Just before transfection, all cells were pooled in one flask and counted (concentration should be around 40×10$^4$ per ml.) 11×4×10$^6$ cells for 10 transfection reactions were spun down in 50 ml conical tubes. Cells were washed 1× with half of the original volume of PBS, then resuspended in 44 ml prewarmed fresh Jurkat media (90% RPMI 1640, 10% FBS, 1% L-glutamate, 1% penicillin/streptomycin) so final concentration was 1×10$^6$/ml. 4 ml of the cells was pipetted in each of the wells in 6-well plates. 2.5 $\mu$l of 2 mg/ml plasmid (pCAT3e series) was pipetted in a 1.5 ml tube, 147.5 $\mu$l RPMI 1640 medium (no serum, no antibiotics) was added, then 20 $\mu$l of the Superfact reagent from Qiagen was added to the plasmid/medium solution, mix by pipetting up and down 5×, and allowed to sit at room temperature for 5–10 min. The transfection complex was added drop-wise to the cells in each well, gently swirling the plate to mix. The cells were incubated in a 37° C., 5% CO$_2$ incubator, and harvested for CAT assay after 24 hours. If oligos were to be added after transfection, 50 $\mu$l of the stock 400 $\mu$M oligo was added to the cells at the designated time, (1 hour after transfection) and cells were returned to the incubator.

CAT Assay

After 24 hours of incubation, cells were harvested by pipetting the cells from each well to 15 ml conical tubes, making sure to rinse well with cell media so no cells were left behind. They were spun at 2,000 rpms for 5 minutes at room temperature. Media was pipetted off. Each cell pellet was washed 3× with 2 ml PBS (PBS was added, vortexed, spun, media pipetted off). As much of the final PBS wash as possible was removed with a pipette tip. 400 $\mu$l of 1× Reporter Lysis Buffer (Promega CAT Enzyme Assay System) was added to each cell pipette, and transferred to a 1.5 ml tube. The cell pellet was incubated in lysis buffer at room temp. for 30 min, vortexed occasionally. These tubes were heated at 60° C. for 10 min at the end of 30 min incubation, then spun at room temp, 12,000 rpms, 2 min, supernatant (lysate) was pipetted to a fresh 1.5 ml tube. For each CAT assay reaction, 100 $\mu$l of the lysate was used, the rest was frozen at −80° C. Each CAT assay was set up as follows: 18.5$\mu$. of water was combined with 100 $\mu$l of lysate, 5 $\mu$l of 5 mg/ml n-Butyryl CoA (Promega) and 1.5 $\mu$l of 0.1 $\mu$Ci/$\mu$l chloramphenicol-$^{14}$C (ICN) in a 1.5 ml tube (total volume 125 $\mu$l) and incubated at 37° C. for 1 hour. At the end of 1 hour, 300 $\mu$l of Xylene (ICN) was added to each tube, vortexed vigorously for 5 sec, spun at full speed for 3 min at room temp., 280 $\mu$l of the upper (xylene) phase was pipetted to a fresh tube. 100 $\mu$l of 0.25 M Tris, pH 8.0, was added to the 280 $\mu$l xylene phase, vortexed, and spun as above. 200 $\mu$l of the upper phase was pipetted to a scintillation vial, 5 ml of scintillation fluid was added, mixed by inversion, and samples counted in the scintillation counter.

In Vitro Oligonucleotide Stability Extends the Biological Activity of Phosphorothioate oligonucleotides.

Figure 1C:
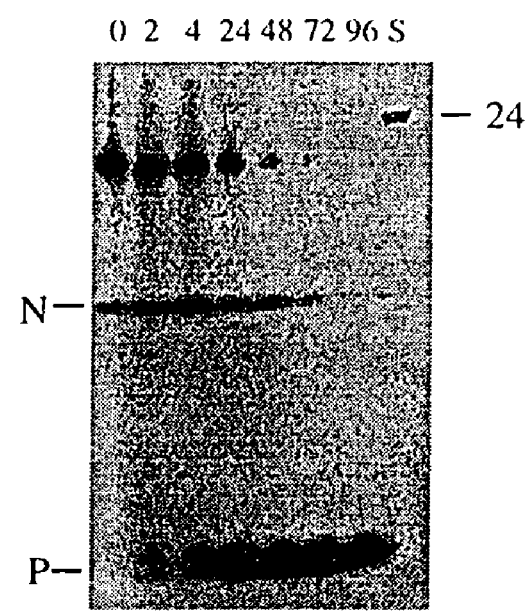
FIGS. 1C and 1D are graphical representations of the in vitro stability of $^{32}$P-labeled phosphorothioate, ICN 16214 (Seq #21), in extracellular fluid and in Jurkat cells, respectively.
Figure 1B:
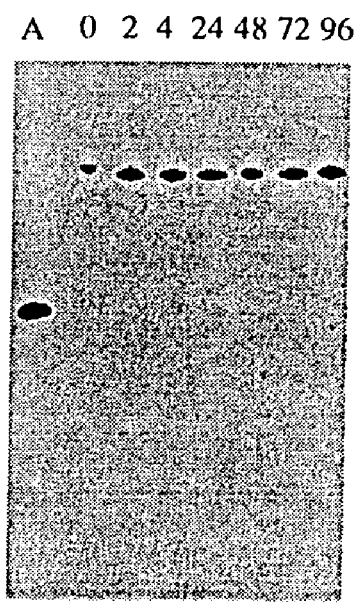
Figure 1D:
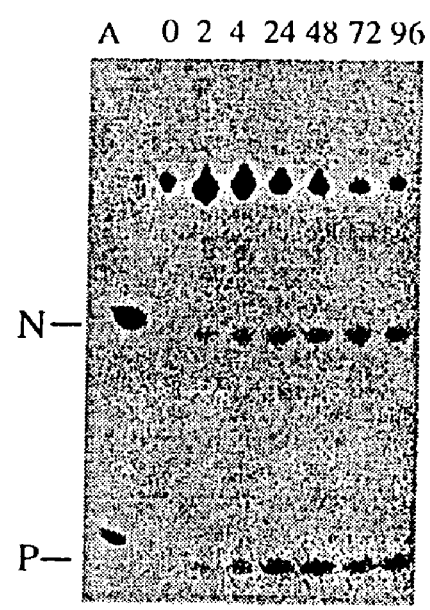
Figure 1E:
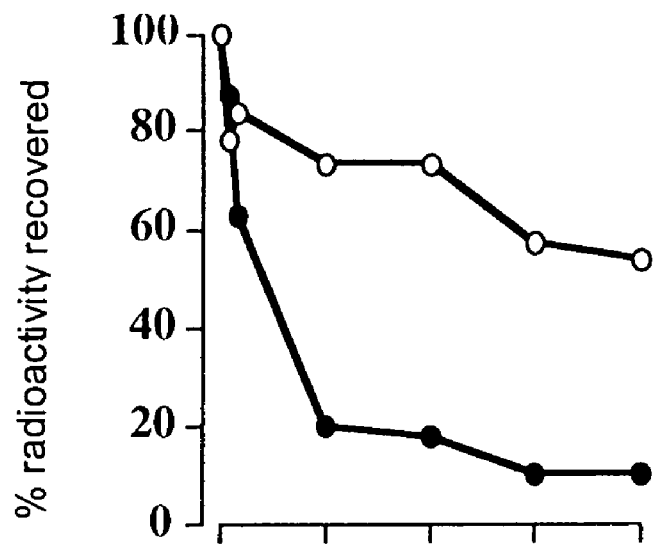
FIGS. 1E and 1F are graphical representations of time-dependent degradation (0–96 h) of each oligonucleotide ICN 16064 (Seq #4) and ICN 16214 (Seq. #21), (2000 cpm) as assessed by electrophoresis on a 20% polyacrylamide denaturing gel followed by visualization using a Phosphorlmager. The percentage of intact full length $^{32}$P-RT03S (○) and $^{32}$P-RTCO6S (●) remaining at each time point, relative to t=0, was determined in eluates from 10000 cpm of extracellular (FIG. 1E) and cell (FIG. 1F) applied through Nickspin columns (Pharmacia). Molecular weight standards (Std), $^{32}$P-dNTP (N) and free $^{32}$P-orthophosphate (P) were simultaneously analysed.
Figure 1F:
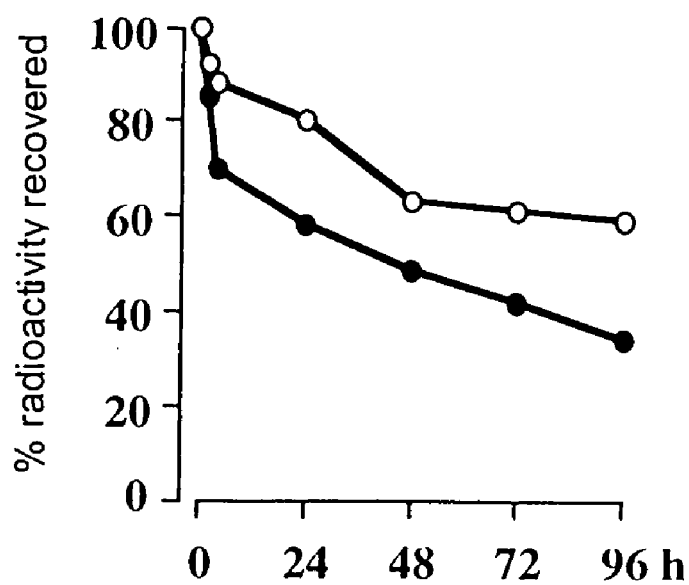

Modification of oligos with phosphorothioate internucleotide linkages can impart nuclease resistance and thus extend the in vitro bioactivity from 1–2 h to 24 h (Stein, (1993) Science 261: 1004–1012). Here, we demonstrated that the G-rich oligo, FIG. 1A, 1B (Seq #4) had greater in vitro stability than a non-G-rich phosphorothioate, FIGS. 1C, 1D (Seq #21). In FIG. 1A the electropherograms clearly show that, for both extracellular 1A (S) and cell 1B (L), considerably more intact $^{32}$P-labeled FIG. 1A (Seq #4) than FIG. 1B (Seq #21) remained following a 96 h incubation with Jurkat cells. Consistent with this observation are the Nickspin column data (FIG. 1B). Here, the percentage of intact oligo recovered from FIG. 1E (Seq #4) after 96 h was 54% (S) and 59% (L) and from FIG. 1F (Seq #21) was 10% (S) and 34% (L). These data suggest that greater nuclease resistance is imparted purely by the presence of G-rich regions in FIG. 1A (Seq #4) and this is presumably associated with the ability of this particular oligo to form folded secondary structures.

Inhibition of Functional CD28 Expression and CD28-Specific IL-2 Production in Activated Human T-Cells by Aptameric Oligonucleotides is Dependent on a Specific G-Rich Motif The relative inhibition of expression of CD28 and CD28-specific IL-2 production by phosphorothioate oligonucleotide sequence # 4 to 21 (5 $\mu$M) from Table 1 is shown in Table 2. Here, we examined the precise sequential requirements for the bioactivity of these aptameric oligonucleotides. Table 2 shows that inhibitory activity was sequence-dependent, in particular, relying on the presence of motif containing two G-quartets separated by four bases (Seq # 5–8). These data suggest that the interaction of an oligo such as FIG. 1A (Seq # 4) and its putative target, is dependent on a precise conformational requirement like that seen in a oligo-protein interaction rather than a nucleic acid: nucleic acid hybridization requirement (as found with antisense and antigene models).

Figure 2:
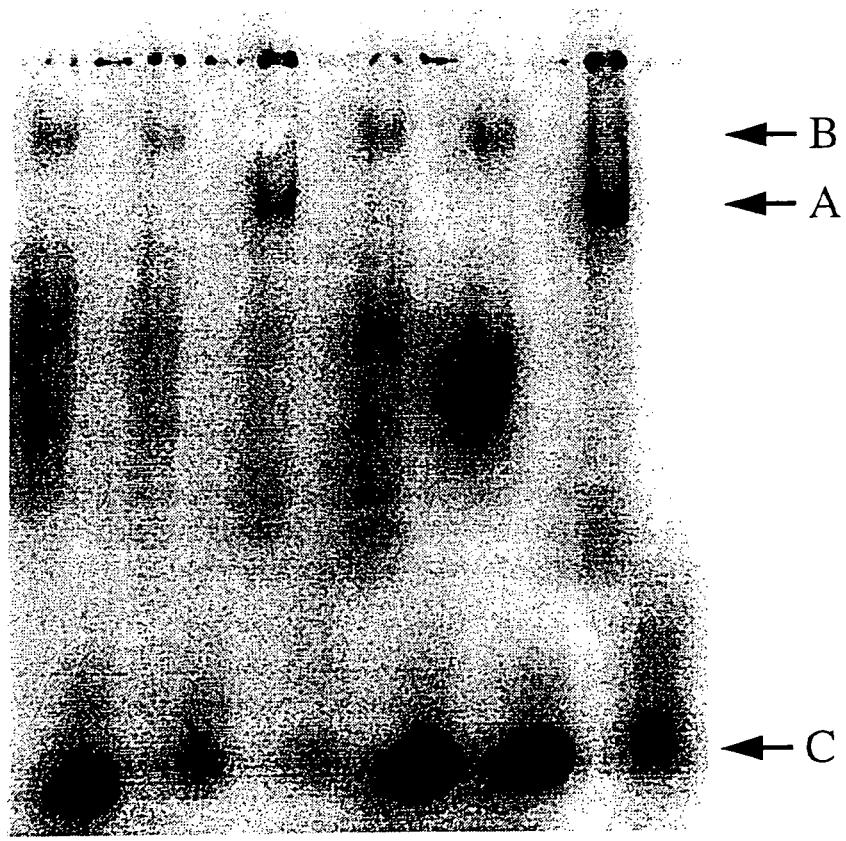
FIG. 2 is a graphical representation of a gel shift analysis which demonstrates that oligonucleotides containing a G-rich 12mer sequence motif (lane 5 and 11) give a distinct band A which differs in electrophoretic shift to band B observed with other phosphorothioate oligonucleotides following incubation with HeLa nuclear extract. Band C is 32P-oligo alone.
Figure 3:
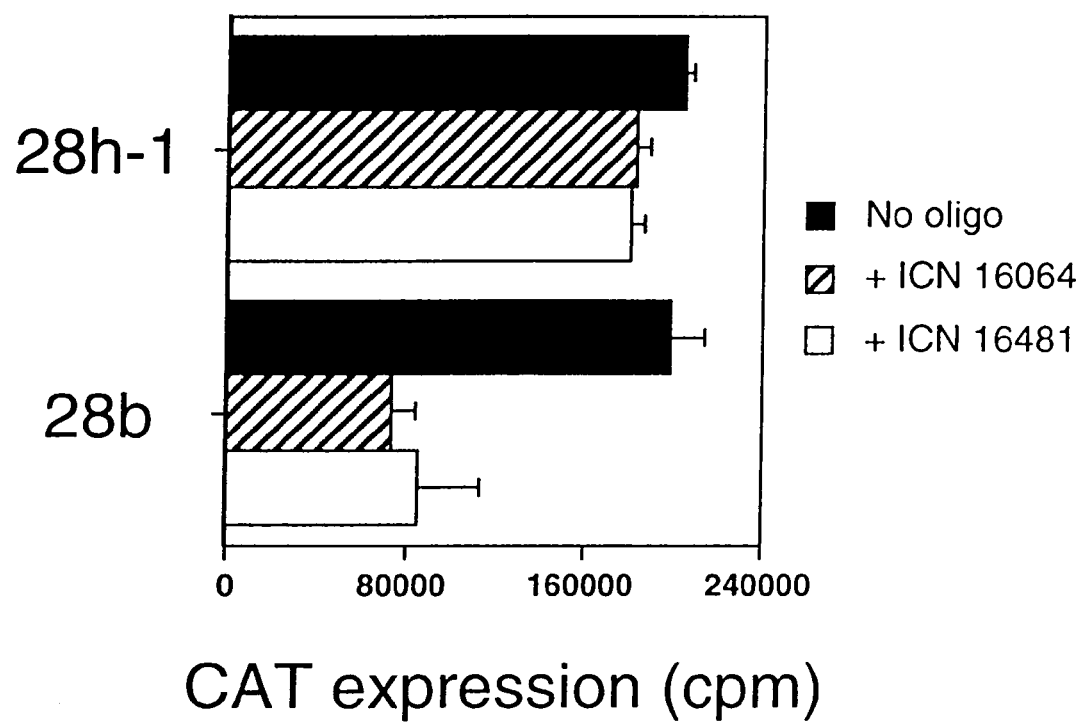
FIG. 3 is a graphical representation of chloramphenicol acetyltransferase (CAT) expression following the transfection of Jurkat cells with plasmid vectors containing a 226 bp insert from the CD28 promoter region (residues −197 to +28) (28b) or a mutant with a substitution at residues −51 to −22 with Seq#3 from Table 1, (28h-1) upstream of the CAT reporter gene, and following treatment with and without the phosphorothioate oligonucleotides, ICN16064 and ICN 16481.

Oligonucleotides Containing a Specific 12mer Sequence Motif Forms a Specific Protein Oligo Complex FIG. 2 shows the electrophoretic mobility shift analysis of 32P-labeled oligonucleotides preincubated with HeLa cell extract. The list of oligos in Table 3 includes two [FIG. 1A (Seq #4) and ICN 16481 (Seq # 5)] which contain a 12mer motif bearing two sets of G-tetrads separated by 4 nucleotides. The motif bearing oligos (lanes 5 and 11 were the only test oligos to give such an oligo-protein shift (Band A) distinct from other phosphorothioate oligos. These data suggest that a specific protein-oligo interaction occurs with oligos containing the 12mer motif.

Inhibition of Functional CD28 Expression in Activated Human T-Cells by Aptameric Oligonucleotides Correlates with Presence of Specific Oligo-Protein Complex Table 4 compares the inhibitory effect on both mitogen-induced CD28 expression and IL-2 production by certain phosphorothioate oligonucleotides at 5 $\mu$M, with their aptameric ability to form a specific oligo-protein complex when incubated with HeLa nuclear extract, an enriched source of transcription factors. These data clearly indicate a correlation between the inhibitory activity of motif-bearing oligos on CD28 expression and IL-2 secretion and the formation of a specific gel shift band. Substitution within the 2 G-tetrads results in loss of function and results in the disappearance of the oligo-protein complex.

The CD28 Upstream Promoter Region –197 to +28 (28b) Binds Sp1

Figure 4:
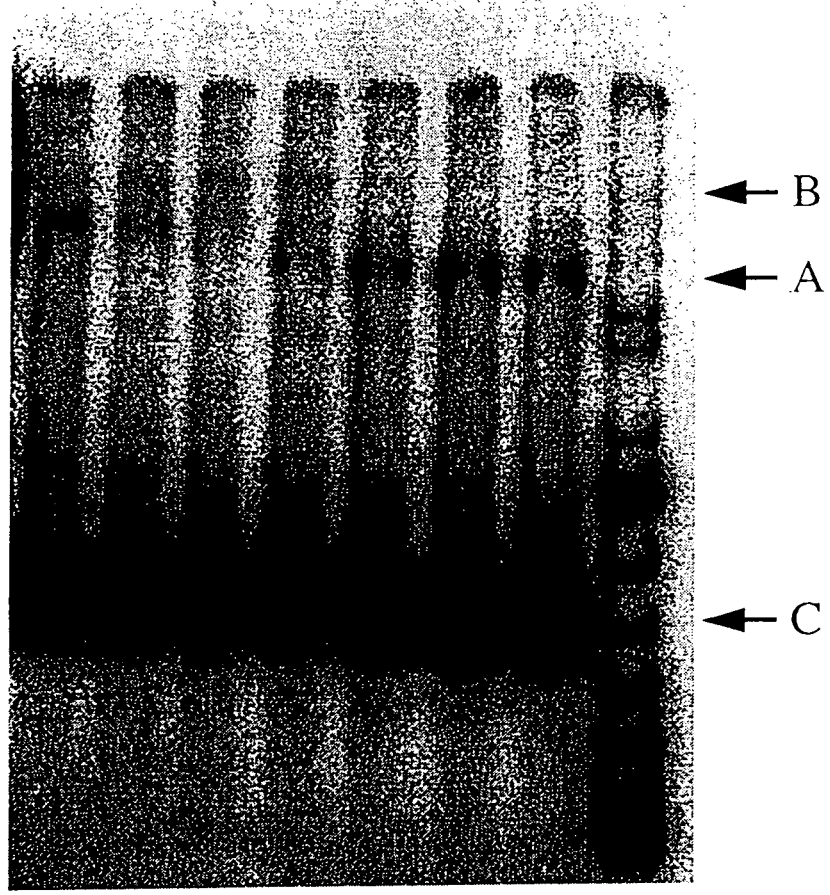
FIG. 4 is a graphical representation of a gel supershift assay showing that the binding of Sp1 to 28b, the upstream region −197 to +28 of the CD28 gene is specific.

$^{32}$P-labeled CD28 promoter region –197 to +28 otherwise known as 28b was incubated with Sp1 protein and serial threefold dilutions of Sp1 antibody beginning with 0.5 $\mu$g. A gel supershift assay was performed and the DNA-protein-antibody complexes resolved following electrophoresis and the data shown in FIG. 4. The data shows that Sp1 does bind to 28b region of the CD28 promoter. This interaction is specific as following serial dilution of the specific Sp1 antibody to 0.00617 ug the Sp1/32P-28b/Sp1 antibody band (band B) disappears leaving the 28b/Sp1 band (band A). This shows the 28b does specifically bind to Sp1. Free 32P-labeled 28b is band C.

An Oligo –51 to –22 Derived from the CD28 Upstream Promoter Region –197 to +28 (28b) and Contains the 12mer G-Rich Motif can Also Bind Sp1

Figure 5:
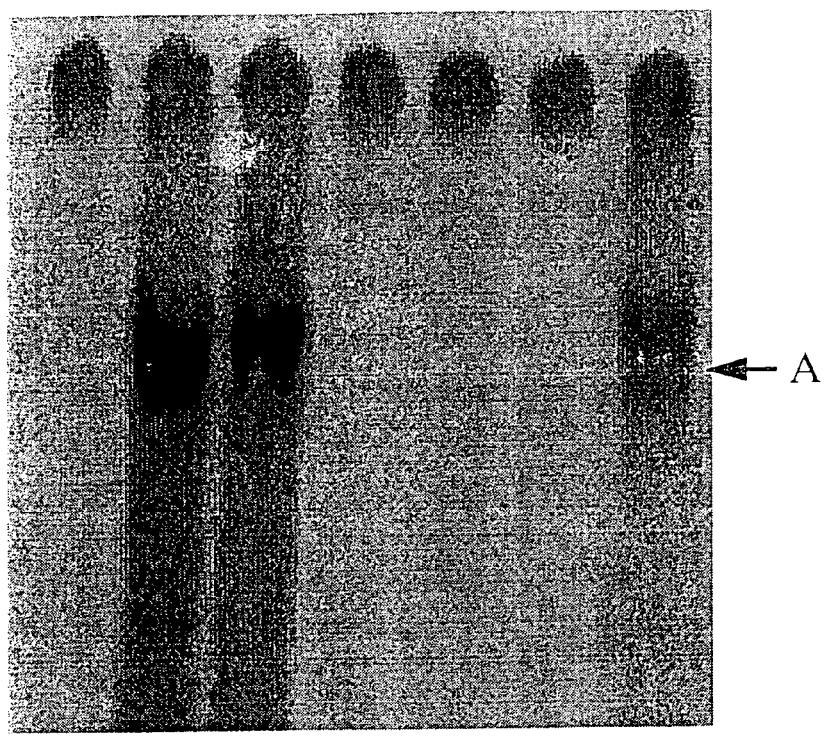
FIG. 5 is a graphical representation of the binding of Sp1 to the $^{32}$P-labeled double stranded oligo 28b (which is derived from the parent 28b—Seq #1 Table 1) and the competition binding of cold double stranded oligo 28b and the aptameric oligos FIG. 1A and 16481.

In an effort to restrict the precise Sp1 binding region in 28b to the G-rich motif in the CD28 promoter region –197 to +28, we synthesized a double stranded (ds) 30mer oligo called 28b oligo (Seq #1 Table 1) which contains the 12mer GGGGAGGAGGGG within its sequence. We hypothesized that this was a Sp1 binding site in the CD28 promoter region. Following 32P-labeling, 28b oligo was incubated with Sp1 extract and indeed they bind to each other (FIG. 5, band A, lane 2 and 3). Competition with cold ds 28b oligo caused the band to disappear showing indeed that the binding was specific to Sp1 (lane 4). Surprisingly, the single stranded phosphorothioate G-rich oligos, FIG. 1A (lane 5) and 16481 (lane 6) (both which contain the G-rich motif) but not the control oligo ICN 16476 (lane 7) competed for binding to Sp 1. This data shows that indeed the phosphorothioate G-rich oligos, FIG. 1A and ICN 16481 can act as aptamers in binding to the DNA binding site of Sp1. The consequence of this interaction is the prevention of Sp1 binding to the Sp1 site at –51 to –22 in the promoter region and which inhibits Sp1-mediated transcription of the CD28 gene and decreases expression of the mature CD28 protein.

Thus, aptamers and methods of modulating an immune response utilizing such aptamers have been disclosed. While specific embodiments have been disclosed herein, the scope of the invention is not be limited except through interpretation of the appended claims.

TABLE 1

| Seq. No. | Oligo ID | Sequence | |
|---|---|---|---|
| 1 | 28b | 5' | GGG TTC CTC GGG GAG GAG GGG CTG GAA CCC |
| | | 3' | CCC AAG GAG CCC CTC CTC CCC GAC CTT GGG |
| 2. | 28h | 5' | GGA GCA CAG GGT GCT |
| | | 3' | CCT CGT GTC CCA CGA |
| 3. | 28h-1 | 5' | TCA TCA CAG GGT GCT |
| | | 3' | AGT AGT GTC CCA CGA |
| 4 | ICN 16064 | 5' | TTG GAG GGG GTG GTG GGG |
| 5 | ICN 16481 | 5' | GGG GAG GAG GGGCTG GAA |
| 6 | ICN 16065 | 5' | GGG TTG GAG GGG GTG GTG GGG |
| 7 | ICN 16475 | 5' | TTG GAG GGG GAG GAG GGG |
| 8 | ICN 16479 | 5' | TTG GAG GGG GAG GTG GGG |
| 9 | ICN 16480 | 5' | TTG GAG GCG GTG GTG GCG |
| 10 | ICN 16538 | 5' | TTG GAG CCG GTG GTG GCC |
| 11 | ICN 16539 | 5' | TTG GAG GGG CTC CTC GGG |
| 12 | ICN 16523 | 5' | TTG GAG CCG GTG GTG G |
| 13 | ICN 16525 | 5' | GGG GTG GTG GGG |
| 14 | ICN 16526 | 5' | G GGG TTG GGG |
| 15 | ICN 16483 | 5' | TG GGG |
| 16 | ICN 16482 | 5' | G GGG |
| 17 | ICN 16527 | 5' | CAC TGC GGG GAG GGC TGG GG |
| 18 | ICN 16528 | 5' | ATG GGG TGC ACA AAC TGG GG |
| 19 | ICN 16487 | 5' | AAC GTT GAG GGG CAT |
| 20 | ICN 16476 | 5' | TTC CAG CCC CTC CTC CCC |

TABLE 1-continued

| Seq. No. | Oligo ID | Sequence |
|---|---|---|
| 21 | ICN 16214 | 5' AAC CTC CCC CAC CAC CCC |
| 22 | SP1 | 5' ATT CGA TCG GGG CGG GGC GAG C |
|  |  | 3' TAA GCT AGC CCC GCC CCG CTC G |
| 23 | AP1 (c-jun) | 5' CGC TTG ATG AGT CAG CCG GAA |
|  |  | 3' GCG AAC TAC TCA GTC GGC CTT |
| 24 | AP2 | 5' GAT CGA ACT GAC CGC CGG CCC CT |
|  |  | 3' CTA GCT TGA CTG GCG GCC GGG GA |
| 25 | NF-KB | 5' AGT TGA GGG GAC TTT CCC AGG C |
|  |  | 3' TCA ACT CCC CTG AAA GGG TCC G |
| 26 | OCT1 | 5' TGT CGA ATG CAA ATC ACT AGA A |
|  |  | 3' ACA GCT TAC GTT TAG TGA TCT T |
| 27 | CREB | 5' AGA GAT GCC CTG ACG TCA GAG AGC TAG |
|  |  | 3' TCT CTA CGG GAC TGC AGT CTC TCG ATC |
| 28 | TFIID | 5' GCA GAG CAT ATA AGG TGA GGT AGG A |
|  |  | 3' CGT CTC GTA TAT TCC ACT CCA TCC T |

TABLE 2

Identification of oligonucleotide sequence responsible for inhibition of CD28 expression and CD28-dependent IL-2 production

| Oligo ID | Sequence | *Relative inhibition of expression CD28 | IL-2 |
|---|---|---|---|
| ICN 16064 | TTG GAG GGG GTG GTG GGG | 100 | 100 |
| ICN 16481 | GGG GAG GAG GGGCTG GAA | 100 | 100 |
| ICN 16065 | GGG TTG GAG GGG GTG GTG GGG | 100 | 100 |
| ICN 16475 | TTG GAG GGG GAG GAG GGG | 100 | 100 |
| ICN 16479 | TTG GAG GGG GAG GTG GGG | 100 | 100 |
| ICN 16480 | TTG GAG GCGGTG GTG GCG | 31 | 38 |
| ICN 16538 | TTG GAG C CG GTG GTG GC C | 40 | 57 |
| ICN 16539 | TTG GAG GGG CTC CTCGGG | 44 | 25 |
| ICN 16523 | TTG GAG CCG GTG GTG G | 38 | 57 |
| ICN 16525 | GGG GTG GTG GGG | 100 | 120 |
| ICN 16526 | G GGG TTG GGG | 30 | 39 |
| ICN 16483 | TG GGG | 2 | 2 |
| ICN 16482 | G GGG | 2 | 2 |
| ICN 16527 | CAC TGC GGG GAG GGC TGG GG | 58 | 76 |
| ICN 16528 | A TG GGG TGC ACA AAC TGG GG | 51 | 63 |
| ICN 16487 | AAC GTT GAG GGG CAT | 26 | 52 |
| ICN 16476 | TTC CAG CCC CTC CTC CCC | 29 | 22 |
| ICN 16214 | AAC CTC CCC CAC CAC CCC | 4 | 2 |

A 12 mer sequence containing two G quartets separated by four bases confers oligo activity. The minimal sequence required for in vitro activity of ICN 16064 was determined by the ability of sequential changes (in bold) to affect ICN 16064-mediated inhibition of CD28 expression in anti-CD3/PMA-activated human T cells and their effect on activated IL-2 production in Jurkat T cells.
*Results are expressed relative to the activity of 5 μM ICN 16064 (100%) whose range of inhibition in seven experiments was 52–79% of CD28 expression and 76–89% of IL-2 production.

TABLE 3

Nuclear extract protein-binding profiles of phosphorothioate oligos (see FIG. 2)

| Oligo | Sequence | Lane No. |
|---|---|---|
| ICN 16064 | TTG GAG GGG GTG GTG GGG | 11, 12 |
| ICN 16481 | GGG GAG GAG GGG CTG GAA | 5, 6 |
| ICN 16480 | TTG GAG GCG GTG GTG GCG | 7, 8 |
| ICN 16538 | TTG GAG CCG GTG GTG GCC | 1, 2 |
| ICN 16485 | GTT GGA GAC CGG GGT TGG | 3, 4 |
| ICN 16476 | TTC CAG CCC CTC CTC CCC | 9, 10 |

TABLE 4

Inhibition of Functional CD28 Expression Correlates With
the Presence of Specific Oligo-Protein Complex

| Oligo | Sequence | Relative inhibition of expression (%) CD28 | IL-2 | Oligo/ protein complex |
|---|---|---|---|---|
| ICN 16064 | TTG GAG <u>GGG GTG GTG GGG</u> | 100 | 100 | Yes |
| ICN 16481 | <u>GGG GAG GAG GGG</u> CTG GAA | 100 | 100 | Yes |
| ICN 16480 | TTG GAG <u>GCG GTG GTG GCG</u> | 31 | 38 | No |
| ICN 16538 | TTG GAG <u>CCG GTG GTG GCC</u> | 40 | 57 | No |
| ICN 16485 | GTT GGA GAC CGG GGT TGG | 11 | 15 | No |
| ICN 16476 | TTC CAG CCC CTC CTC CCC | 29 | 22 | No |
| ICN 16214 | AAC CTC CCC CAC CAC CCC | 4 | 2 | No |

What is claimed is:

1. An aptamer having a length of no more than 22 nucleotides and having the sequence 5' GGG GAG GAG GGG CTG GAA 3' (SEQ ID NO: 5).

2. An aptamer having a length of no more than 22 nucleotides and having the sequence 5' TTG GAG GGG GAG GAG GGG 3' (SEQ ID NO: 7).

3. An aptamer having a length of no more than 22 nucleotides and having the sequence 5' TTG GAG GGG GAG GTG GGG 3' (SEQ ID NO: 8).

4. A method of treating an isolated immunecompetent cell, comprising administering to the cell an aptamer at a concentration effective to reduce CD28 expression, wherein the aptamer is selected from the group consisting of SEQ ID NO: 5, SEQ ID NO: 7, and SEQ ID NO: 8.

5. The method of claim 4 wherein the immunecompetent cell is from a patient suffering from a graft vs host response.

6. The method of claim 4 wherein the immunecompetent cell is from a patient suffering from an autoimmune disease.

7. The method of claim 6 wherein the autoimmune disease comprises rheumatoid arthritis.

8. The method of claim 6 wherein the autoimmune disease comprises multiple sclerosis.

9. The method of claim 6 wherein the autoimmune disease comprises lupus erythematosus.

10. The method of claim 6 wherein the autoimmune disease comprises insulin dependent diabetes mellitus.

11. The method of claim 6 wherein the autoimmune disease comprises psoriasis.

* * * * *